United States Patent
Brown (10) Patent No.: US 10,395,006 B2
(45) Date of Patent: Aug. 27, 2019

(54) CENTRALIZED EOB ARCHIVING AND ACCESS

(71) Applicant: ALEGEUS TECHNOLOGIES, LLC, Waltham, MA (US)

(72) Inventor: Steven T. Brown, Franklin, WI (US)

(73) Assignee: Alegeus Technologies, LLC, Waltham, MA (US)

( * ) Notice: Subject to any disclaimer, the term of this patent is extended or adjusted under 35 U.S.C. 154(b) by 54 days.

(21) Appl. No.: 14/640,293

(22) Filed: Mar. 6, 2015

(65) Prior Publication Data

US 2015/0178454 A1 Jun. 25, 2015

Related U.S. Application Data

(63) Continuation of application No. 11/627,113, filed on Jan. 25, 2007, now abandoned.

(51) Int. Cl.
| | |
|---|---|
| *G06Q 40/00* | (2012.01) |
| *G06F 19/00* | (2018.01) |
| *G06Q 10/08* | (2012.01) |
| *G06Q 40/08* | (2012.01) |
| *G06Q 50/22* | (2018.01) |
| *G06Q 50/24* | (2012.01) |

(Continued)

(52) U.S. Cl.
CPC ......... *G06F 19/328* (2013.01); *G06Q 10/087* (2013.01); *G06Q 40/08* (2013.01); *G06Q 50/22* (2013.01); *G06Q 50/24* (2013.01)

(58) Field of Classification Search
None
See application file for complete search history.

(56) References Cited

U.S. PATENT DOCUMENTS

| | | | | |
|---|---|---|---|---|
| 5,930,759 A | * | 7/1999 | Moore | B42D 15/00 283/117 |
| 6,208,973 B1 | * | 3/2001 | Boyer | G06Q 20/02 705/2 |
| 6,343,271 B1 | | 1/2002 | Peterson et al. | |

(Continued)

OTHER PUBLICATIONS

International Preliminary Report on Patentability and Written Opinion for International Application No. PCT/US2008/052102, dated Aug. 4, 2008.

(Continued)

*Primary Examiner* — Jason Borlinghaus
(74) *Attorney, Agent, or Firm* — Foley & Lardner LLP; Christopher J. McKenna (57) ABSTRACT

Methods and systems provide substantiation proof of claims made against medical spending accounts. Medical-insurance adjudication explanations are received at a benefits-records system, specifying a medical-insurance claim submitted to a medical insurer and identifying an adjudication decision of the medical insurance claim. The medical-insurance adjudication explanations are stored in a common format. A request is received from an insured party to apply a payment amount to a medical spending account. The payment amount corresponds to an expense associated with a medical-insurance claim submitted to one of the medical insurers but not paid. The request is posted to a third-party administrator with information from the corresponding medical-insurance adjudication explanations.

18 Claims, 6 Drawing Sheets

(51) Int. Cl.
*G06Q 10/00* (2012.01)
*G06Q 50/00* (2012.01)

(56) References Cited

U.S. PATENT DOCUMENTS

| | | | |
|---|---|---|---|
| 7,711,660 B1 | 5/2010 | Gentile et al. | |
| 7,942,328 B2* | 5/2011 | Snyder | G06K 7/10544 |
| | | | 235/375 |
| 2004/0006490 A1* | 1/2004 | Gingrich | G06F 19/328 |
| | | | 705/2 |
| 2006/0036523 A1 | 2/2006 | Stover et al. | |
| 2007/0005402 A1 | 1/2007 | Kennedy et al. | |
| 2007/0005403 A1 | 1/2007 | Kennedy et al. | |
| 2007/0061393 A1* | 3/2007 | Moore | G06F 17/3089 |
| | | | 709/201 |
| 2008/0046292 A1* | 2/2008 | Myers | G06F 17/30557 |
| | | | 705/3 |

OTHER PUBLICATIONS

U.S. Office Action received in U.S. Appl. No. 11/627,113, dated Aug. 5, 2010.
U.S. Office Action received in U.S. Appl. No. 11/627,113, dated Apr. 20, 2011.
U.S. Office Action received in U.S. Appl. No. 11/627,113, dated Sep. 8, 2014.

* cited by examiner

InsuranceCorp

EXPLANATION OF BENEFITS

JOHN A SMITH
123 MAIN ST
MOUNTAIN CITY CA 90224

| Date | Patient | Service | Provider | Charge | Excluded | Copay | Benefit | Payment |
|---|---|---|---|---|---|---|---|---|
| 1/6/06 | JOHN A SMITH | PROPHYLAXIS | KEN JONES DDS | $120.00 | $35.00 | $10.00 | 100% | $75.00 |
| 1/9/06 | MARY B SMITH | URG ONLAY REPAIR | KEN JONES DDS | $252.00 | $42.00 | $10.00 | 80% | $160.00 |
| 2/1/06 | MARY B SMITH | ORTHO | ANN BLACK DDS | $450.00 | $0.00 | $25.00 | 50% | $212.50 |

Total Payment $447.50

CENTRALIZED EOB ARCHIVING AND ACCESS

CROSS-REFERENCES TO RELATED APPLICATIONS

This application claims the benefit of priority under 35 U.S.C. § 120 as a continuation of U.S. patent application Ser. No. 11/627,113, filed Jan. 25, 2007, which is hereby incorporated by reference herein in its entirety.

BACKGROUND OF THE INVENTION

This application relates generally to medical spending accounts. More specifically, this application relates to the use of centralized repositories in managing insurance information used to support reporting requirements associated with medical spending accounts.

There are currently a variety of different types of medical spending accounts. These different accounts are managed in different ways and are generally used for different purposes, but have as a common factor that they permit funds earned through employment to be applied on with certain income-tax advantages to pay for certain medical expenses. "Medical" expenses include expenses that arise in the diagnosis or treatment of conditions in the human body, including teeth or other oral structures in the form of dental expenses and including the eye and other ophthalmic structures in the form of vision expenses. Medical expenses may include fees to be paid to physicians, dentists, optometrists, or other medical practitioners for their services directly, fees paid to laboratories who perform analyses of blood or other tissues or who operate diagnostic equipment like x-ray machines, magnetic-resonance-imaging machines, and the like.

Different types of medical spending accounts available for these types of uses in the United States currently include flexible spending accounts ("FSAs"), health savings accounts ("HSAs"), and health reimbursement accounts ("HRAs"), and other types of medical spending accounts may be developed in the future. FSAs are financial accounts that are established as part of employer-sponsored benefits plans. Employees are able to contribute a set annual amount to the accounts, usually as part of a regular salary deduction that is applied to each paycheck. The employee is then able to spend the funds from the accounts to pay for medical expenses. Often the annual amount can be spent before the employee has completed making the contributions, permitting payment for medical expenses effectively to be made on an interest-free credit basis. Because the contributions to the account are made as a salary reduction, they are not subject to income tax.

HSAs are financial accounts that are intended to provide for payment of unreimbursed medical expenses incurred by those who are self-employed or employed by small organizations (fewer than 50 employees). One qualification requirement for such accounts is that the employee be covered by a high-deductible insurance plan. Funds in the account can be used on a pre-income-tax basis to pay for certain medical-insurance premiums and can earn tax-deferred interest. Unlike with FSAs, the funds in HSAs are available to rolled over from year to year if they are unused.

HRAs are financial accounts having funds that are set aside by employers to provide reimbursement for employees who incur medical expenses. Like HSAs, the funds in the account can be rolled over from year to year, but they differ from HSAs not only in the fact that it is the employer who funds them rather than the employee, but also in that they have no restrictions on the size of the company where they are offered. The tax advantage for such accounts is enjoyed by the employers, who qualify for preferential tax treatment in a manner similar to employers who fund insurance plans.

In addition to their individual features, each of these different kinds of accounts may also be used in combination with different insurers. This may occur as an employee incurs medical expenses, some of which are eligible for reimbursement by an insurer and others of which are paid from one of the different types of medical spending accounts. Employees of different organizations, even those who reside within a single household, may interact with different insurers. Even a single employee frequently interacts with different insurers, particularly for different types of treatments. While this versatility makes for a flexible environment in which different types of medical spending accounts and different insurers may be used to accommodate individual circumstances, it also creates an environment in which management of relevant information may be difficult. Different insurers have different ways and formats for reporting how they determined which expenses are eligible for reimbursement, different ways for questioning and/or appealing those decisions, and the like. And the reporting requirements to comply for the tax benefits of the different types of accounts with the Internal Revenue Service differ. This reporting is further complicated by the different reporting formats used by the insurers.

There is thus a general need in the art for improved mechanisms for organizing insurance and/or medical spending account information for use by employees, administrators, and others.

BRIEF SUMMARY OF THE INVENTION

Embodiments of the invention provide a central repository that maintains adjudication records of medical insurance claims in a standard format. This repository may act as a conduit for efficiently coordinating requests by insured parties to have access to the adjudication records and to initiate requests for application of amounts not covered by insurance to medical spending accounts. At the same time, the standard format of the records permits efficient transmittal of such requests to third-party administrators with substantiation documentation that meets reporting requirements.

Thus, methods of the invention provide substantiation proof of claims made against medical spending accounts. A plurality of medical-insurance adjudication explanations are received at a benefits-records system. Each such medical-insurance adjudication explanation comprises a specification of a medical-insurance claim submitted to one of a plurality of medical insurers and identifies an adjudication decision of the medical insurance claim. Each of the plurality of medical-insurance adjudication explanations is stored in a common format. A request is received from an insured party to apply a payment amount to a medical spending account. The payment amount corresponds to an expense associated with a medical-insurance claim submitted to one of the plurality of medical insurers and identified in one of the medical-insurance adjudication explanations as not paid by the one of the medical insurers. The request is posted to a third-party administrator with information from the one of the medical-insurance adjudication explanations.

There are different ways in which the information may be posted to the third-party administrator. For example, in some embodiments, the information comprises the one of the medical-insurance explanations itself Such a medical-insurance explanation may comprise an optically readable code, such as a bar code, that summarizes details of the medical-insurance claim. In an alternative embodiment, the information may be a subset of information extracted from the one of the medical-insurance adjudication explanations. In certain embodiments, the common format itself may include an optically readable code summarizing details of the medical-insurance claim comprised in respective ones of the medical-insurance adjudication explanations.

There are also different ways in which the plurality of medical-insurance adjudication explanations may be received. For instance, in one embodiment, at least one of them is received from one of the medical insurers. In another embodiment, at least one of them is received from a party insured by one of the medical insurers. The information may be received over a public network. In certain embodiments, the at least one of the medical-insurance adjudication claims is converted into the common format. Examples of medical spending accounts that may be involved in these methods include flexible spending accounts, health savings accounts, and health reimbursement accounts, among others.

The methods of the invention may be embodied in a system having a communications device, a storage device, a processor, and a memory coupled with the processor. The plurality of medical-insurance adjudication explanations are stored on the storage device. The memory comprises a computer-readable medium having a computer-readable program embodied therein for directing operation of the system. The computer-readable program includes instructions for operating the system in accordance with the various embodiments described above.

BRIEF DESCRIPTION OF THE DRAWINGS

A further understanding of the nature and advantages of the present invention may be realized by reference to the remaining portions of the specification and the drawings wherein like reference numerals are used throughout the several drawings to refer to similar components. In some instances, a sublabel is associated with a reference numeral and follows a hyphen to denote one of multiple similar components. When reference is made to a reference numeral without specification to an existing sublabel, it is intended to refer to all such multiple similar components.

DETAILED DESCRIPTION OF THE INVENTION

Embodiments of the invention provide methods and systems for generating and storing benefits-determination information that may be provided by a variety of different insurers. Such benefits-determination information is generally provided by an insurer in the form of an "Explanation of Benefits" ("EOB") statement that is transmitted in response to a request for payment and a decision by the insurer on the request. In different instances, the determination made by the insurer is prompted by receipt of a claim from an insured party or by receipt of a claim from a medical-services provider. When a claim is submitted by an insured party, it is usually submitted because the insured party has received and paid for medical services and therefore takes the form of a reimbursement request. When a claim is submitted by a medical-services provider, it is usually submitted because the provider has provided services to an insured party that have not been paid for and therefore takes the form of a request for payment for services previously rendered.

The process by which the insurer determines how to respond to the request is largely the same irrespective of the form that the request takes. Particulars that describe the type of service rendered are evaluated to determine whether they are services covered by the particular policy specifications that apply to the insured party and how those policy specifications apply to that service. The result of this evaluation is a determination of the financial responsibility of the insurer for the services that were performed, with the insurer then issuing a payment for that amount either to the provider or to the insured party depending on who originated the request. An explanation of how the amount was determined is transmitted to the insured party in the form of an EOB statement.

To accommodate the variety of different forms of EOB statements that may be issued by insurers and to facilitate compliance with the different reporting requirements when information from such EOB statements must be processed by third-party administrators, embodiments of the invention make use of a centralized benefits-records system. This system provides a mechanism for maintaining EOB statements in a consistent manner and as an interface to insured parties and third-party administrators for accessing the statements.

Figure 1:
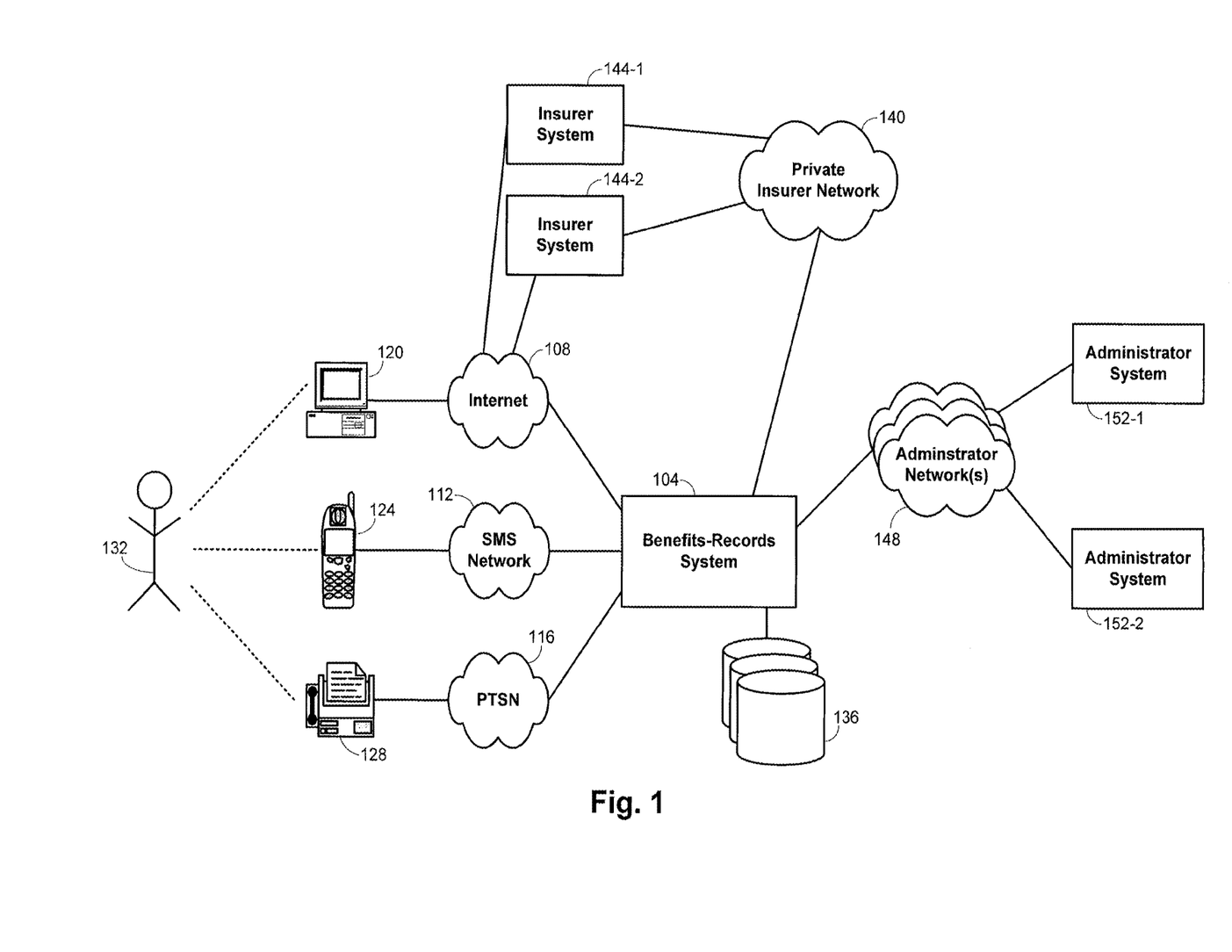
FIG. 1 is a schematic diagram illustrating an architecture within which methods of the invention may be performed.

FIG. 1 provides a schematic illustration of how such a benefits-records system 104 may be integrated within an architecture for processing insurance claims and processing funds payments from medical savings accounts. In this illustration, the benefits-records system 104 comprises a computation system that has software for implementing specific aspects of the invention described below. It is interfaced with one or more storage devices 136 that act as data repositories to store the formatted EOB statements.

Interaction with the benefits-records system 104 may take place through any of a variety of different computational networks, perhaps depending on the nature of the party wishing to access the formatted EOB information. For example, in some instances, information may be received directly from an insurer system 144 that is operated on behalf of an insurer. Such information may be directed through a private insurer network 140 whose private nature acts to enhance the security of the private medical and financial information that may be included on the EOB statements.

In other instances, interactions may be made between the benefits-records system 104 and an insured party 132. Such interactions may take place as the insured party 132 wishes to access past EOB information as explained below. It may also take place to provide a mechanism by which the insured party 132 transmits EOB statements directly to the benefits-records system. Such transmission from the insured party 132 may be appropriate when the insurer sends EOB statements directly to the insured party 132 or is otherwise not equipped to transmit such statements directly to the benefits-records system 104.

The drawing illustrates a number of different techniques that the insured party 132 may use for transmission of EOB statements to the benefits-records system, or for other interactions that might be initiated with the benefits-records system 104 as described below. These different techniques permit the insured party 132 to transmit an EOB statements to the system 104 in different ways, which may be beneficial in accommodating different forms in which the EOB statements are provided to the insured party 132. For example, one communications mechanism comprises use of a public network like the Internet 108, with the insured party 132 using a personal computer 120 or other computational device to establish a connection with the public network. Such a communications mechanism is suitable for transmission of a variety of electronic forms of EOB statements, such as statements that are provided in PDF or other electronic formats. Because of the public nature of the Internet, transmissions over it may be subject to any of a variety of security mechanisms to protect the confidential nature of the medical and financial data that may be included in the EOB statements. This includes establishing secure connections, encrypting the transmissions, and the like.

The public-telephone switched network 116 also provides a communications mechanism that may be used for transmission of EOB statements and other information to the benefits-records system 104, particularly in supporting facsimile transmissions from a fax machine 128. This provides a convenient way for transmitting copies of hard-copy statements that insured parties might receive from insurers. While the Internet 108 also provides a mechanism for transmitting copies of hard-copy statements when the statements are scanned into an electronic format, scanners currently remain less available to many insured parties than fax machines 128.

Another communications that may sometimes be used for appropriate forms of the EOB statements is a short-message-service network 112 that supports textual communications from cellular devices like mobile telephones 124, personal digital assistants, and other wireless handheld devices.

The drawing in FIG. 1 shows explicitly that public networks like the Internet 108 provide suitable communications paths to the benefits-record system 104 that may be used by insurer systems 144 as an alternative to the use of private networks. Although not shown explicitly in the drawing, such public networks also permit communications to be made by third-party administrators. The drawing instead shows an embodiment in which separate private administrator networks 148 are used to effect such communications, but this is not a requirement of the invention. Such private networks do have the same benefit as does the use of private networks to interface with insurer systems 144, namely that they provide greater security for the exchange of confidential information than is the case with public networks in the absence of enhanced security protocols.

The administrator networks 148 are provided in communication with administrator systems 152 suitable for operation by third-party administrators in complying with requirements for applying payment amounts the insured party is responsible for to medical spending accounts. For example, third-party administrators may interact with an administration system 152 in processing requests to apply amounts to medical savings accounts and in processing substantiation and authentication documentation related to such requests.

Figure 2:
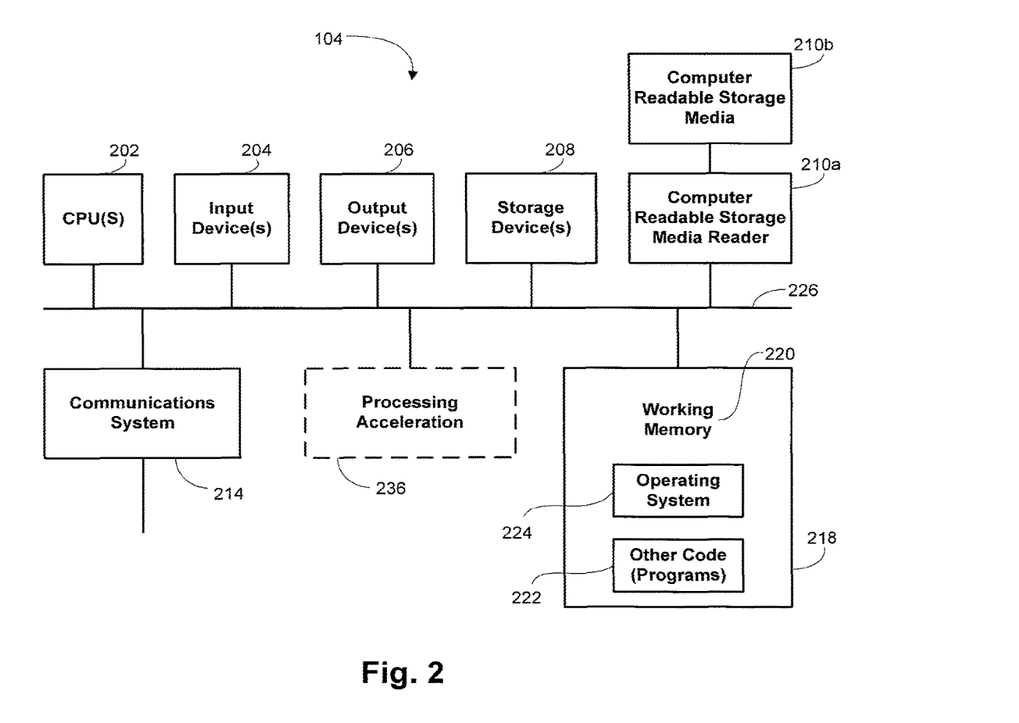
FIG. 2 is a schematic diagram of a computational device on which methods of the invention may be embodied.

FIG. 2 provides a schematic illustration of a physical structure that may be comprised by the benefit-records system 104 to implement embodiments of the invention. FIG. 2 broadly illustrates how individual system elements may be implemented in a separated or more integrated manner. The benefits-records system 104 is shown comprised of hardware elements that are electrically coupled via bus 226, including a processor 202, an input device 204, an output device 206, a storage device 208, a computer-readable storage media reader 210a, a communications system 214, a processing acceleration unit 216 such as a DSP or special-purpose processor, and a memory 218. The computer-readable storage media reader 210a is further connected to a computer-readable storage medium 210b, the combination comprehensively representing remote, local, fixed, and/or removable storage devices plus storage media for temporarily and/or more permanently containing computer-readable information. The communications system 214 may comprise a wired, wireless, modem, and/or other type of interfacing connection and permits data to be exchanged over the architecture described in connection with FIG. 1.

The benefits-records system 104 also comprises software elements, shown as being currently located within working memory 220, including an operating system 224 and other code 222, such as a program designed to implement methods of the invention. It will be apparent to those skilled in the art that substantial variations may be made in accordance with specific requirements. For example, customized hardware might also be used and/or particular elements might be implemented in hardware, software (including portable software, such as applets), or both. Further, connection to other computing devices such as network input/output devices may be employed.

Figure 3:
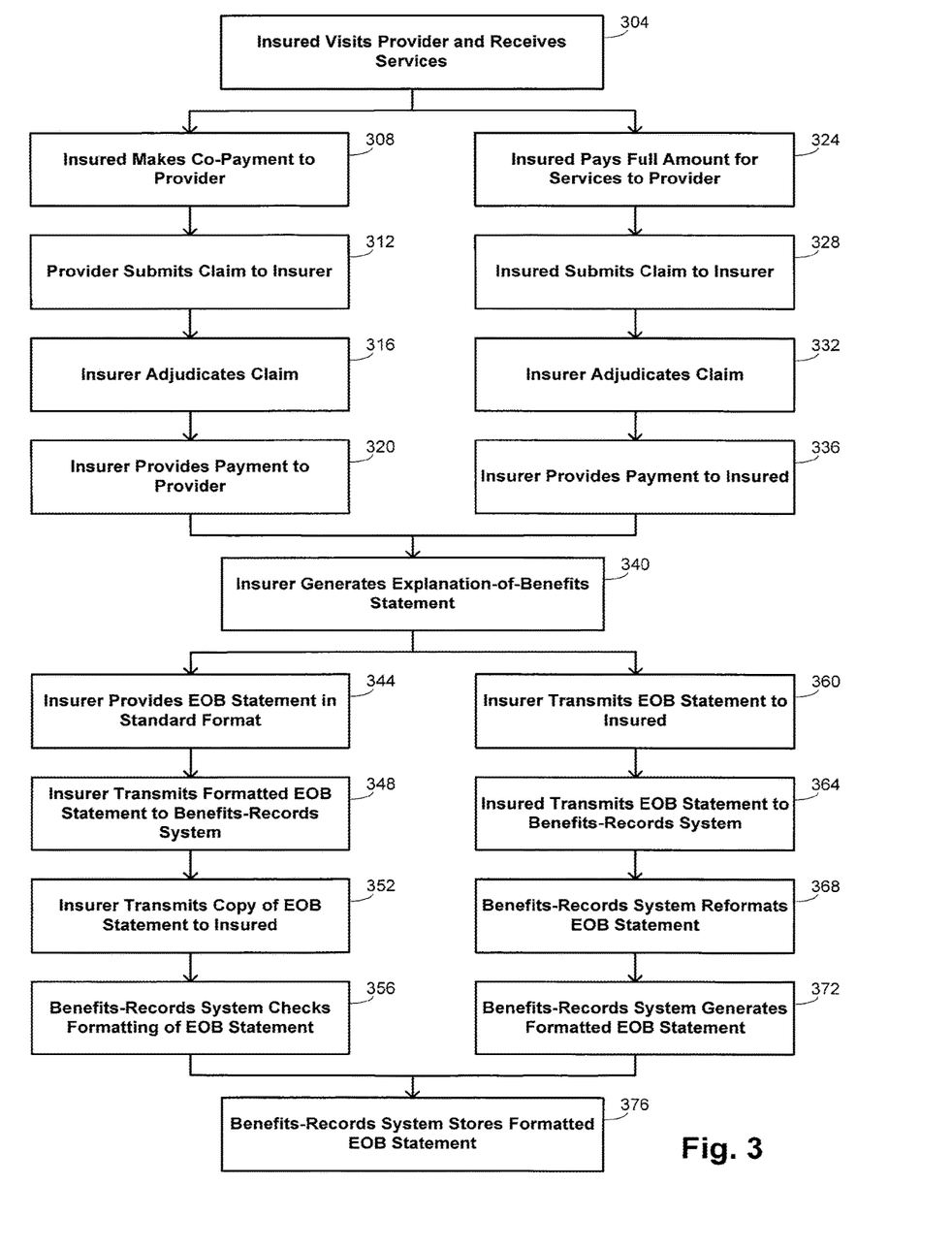
FIG. 3 is a flow diagram summarizing methods of providing EOB statement to a centralized benefits-records system.

Methods by which the benefits-records system 104 may acquire and store formatted EOB statements are summarized with the flow diagram of FIG. 3. Fundamentally, the generation of an EOB statement begins with a visit by the insured party to a medical provider to receive medical services, as indicated at block 304. As previously noted, there are multiple ways in which a claim to the insurer may be made depending on the financial arrangements between the insured party and the provider. This difference is indicated explicitly with two separate prongs in the upper portion of the flow diagram, the left prong corresponding to the case where the insured makes at most a copayment to the provider at block 308. As is well known in the art, a copayment is a contribution for payment of the medical services that is made by the insured party, often required in medical-insurance policies to prevent "moral hazard" as perceived abuses of the otherwise-free availability of medical service. The copayment is usually a relatively small amount, and may vary depending on the type of medical service performed and/or the level of specialization of the provider.

In such instances, it is often the provider who submits the claim to the insurer at block 312 as a request for payment for the medical services that were provided to the insured party. The insurer adjudicates the received claim in accordance with its usual policies at block 316 and, if the claim is proper, provides a payment of an amount dictated by the relevant policy to the provided at block 320. An explanation of how the payment amount was determined by application of the policy terms is generated at block 340 in the form of an EOB statement.

The right prong corresponds to the case where the insured party makes payment in full for the medical services to the provider at block 324 and is the one who submits a claim to the insurer for reimbursement at block 328. The basic action taken by the insurer is the same, namely adjudicating the claim at block 332 to determine the appropriate amount due to be paid by the insurer in accordance with the applicable policy. The subsequent action by the insurer differs under this prong in that the insurer then provides payment directly to the insured at block 336. The EOB that is generated at block 340 in this instance also provides an explanation of how the payment amount was determined through application of the relevant policy terms.

The lower portion of FIG. 3 illustrates methods by which the EOB statement may be provided in a standard format to the benefits-records system 104. The two prongs provide illustrations of different steps that may be executed, often depending on the capabilities of the insurer to provide the EOB in the standard format. For example, in the left prong, the insurer is both capable and willing to provide the EOB statement in a format identified as standard by the benefits-records system 104. The EOB statement is accordingly provided in that format at block 344, with the insurer transmitting the formatted EOB statement directly to the benefits-records system 104 at block 348. A copy of the EOB statement is transmitted to the insured party at block 352. The benefits-records system may verify that the formatting of the EOB statement received from the insurer at block 356, perhaps rejecting the statement if it fails to comply with the specified standard.

In the right prong, the insurer does not necessary provide an EOB statement already in compliance with the standard used by the benefits-records system 104. Also in this prong, the benefits-records system 104 does not receive the EOB statement directly from the insurer, but instead receives it via the insured party, who acts as an intermediary. After the insurer transmits the EOB statement to the insured party at block 360, it may be transmitted by the insured party to the benefits-record system at block 364. This transmission may be made using any of the different mechanisms described in connection with FIG. 1, including electronic transmission of a scanned version of the EOB statement or any other electronic version of the EOB statement, fax transmission, SMS transmission, or the like.

In these instances, the benefits-record system 104 may include a facility for reformatting the EOB statement into the desired standard format at block 368. Implementation of such a reformatting facility may be done in a variety of different ways. For example, the system 104 might be provided with information defining the particular format used for EOB statements by various different insurers. After identifying the source of the EOB statement, this information could be used to extract the relevant data from the statement to generated a corresponding version of the statement in the standardized format at block 372. In cases where the information is difficult to extract because of the quality of the transmitted EOB statement, or where the transmitted EOB statement originates from an insurer for which the system 104 does not have a template, a mechanism may be provided to permit human intervention in examining the transmitted EOB statement.

Generation of the formatted EOB statement at block 372 is thus generally performed by identifying those portions of the transmitted EOB statement that contain the information needed for specified fields in the formatted EOB statement and filling those fields with that information. In some cases, this mapping of information may involve mapping from a single field in the transmitted EOB statement to multiple fields of the formatted EOB statement or may involve mapping from multiple fields in the transmitted EOB statement to a single field in the formatted EOB statement. This may be the case, for example, where the different formats combine information in different ways.

Once the EOB statement has been generated into the standard format, it is stored at block 376 by the benefits-records system on the storage devices 136. This makes the EOB statement accessible with other stored EOB statements for a variety of different uses, some of which are discussed below. The utility of the stored EOB statements is significantly enhanced by both their centralized accessibility and by their standard format.

In some embodiments, part of the standard format in which the EOB statements are stored includes an optically readable code that permits data elements to be extracted from the standardized EOB statement efficiently. Examples of optically readable codes that may be used in different embodiments include linear bar codes, two dimensional bar codes, and the like. An illustration of one format that might be used for a standardized EOB statement in an embodiment is provided in FIG. 4. The identification of certain types of fields in this illustration is not intended to be limiting. In other embodiments, the standardized EOB statement might comprise a smaller or greater number of fields depending on how the centralized repository is implemented.

Figure 4:
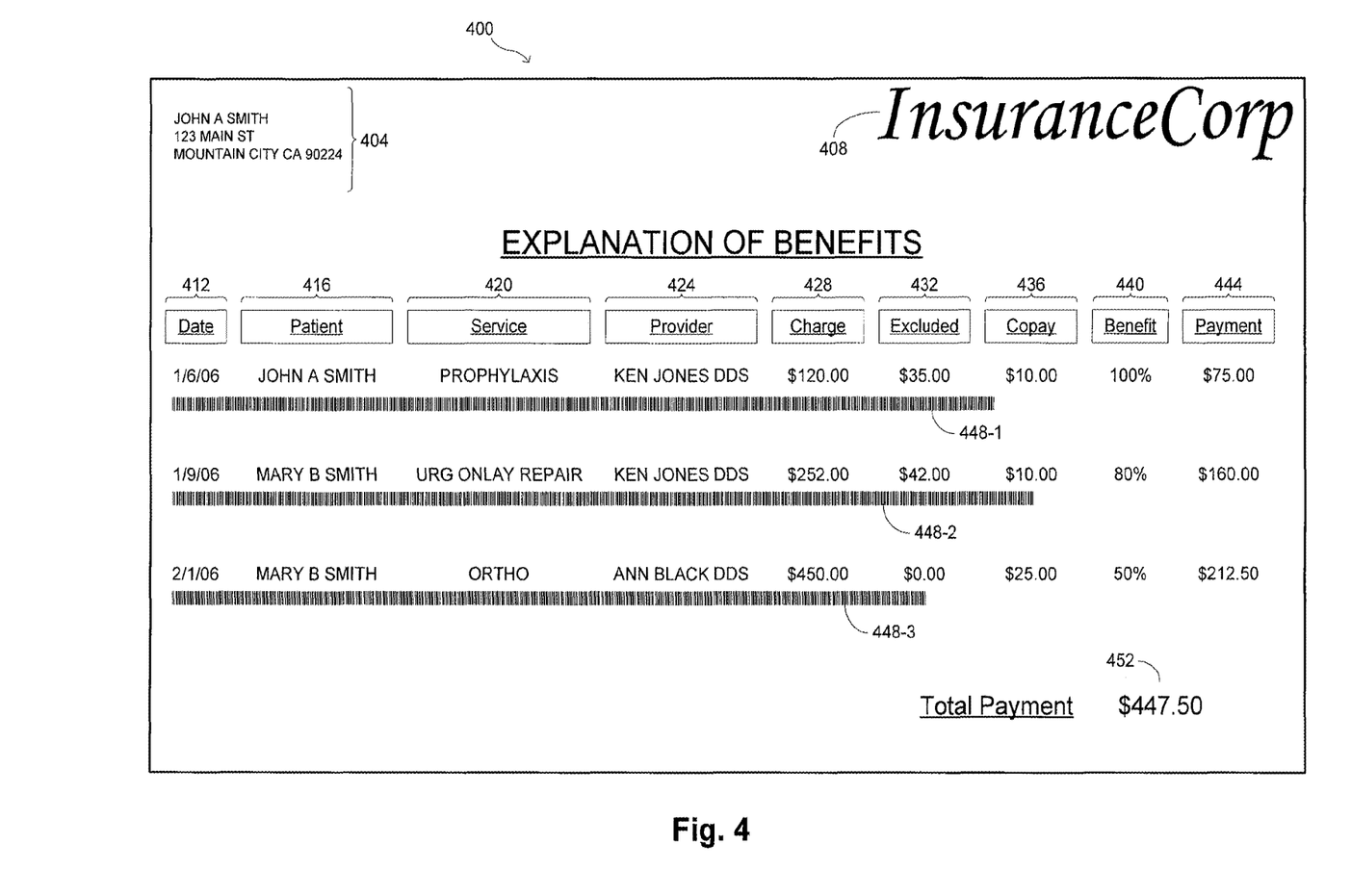
FIG. 4 is an example of an EOB statement that includes optically readable coded indicia in accordance with an embodiment of the invention.

In the example of FIG. 4, the EOB statement 400 includes an identification of the originating insurer 408, who may or may not have generated the EOB statement 400 in the format in which it is stored in by the benefits-records system. The statement 400 also includes an identification of the insured party 404, which is shown in the illustration to include the name and address of the insured party. In other embodiments, other information might be provided, such as telephone number, Social Security Number, insurance identification number, and the like.

Details of the application of benefit information are organized in this illustration in several fields that include a specification of the service(s) that were the subject of a particular claim and the results of the adjudication of that claim. The service(s) are identified by the date 412 they were performed, the patient 416 who received the service, a brief summary of the service 420, and an identification of the provider 424 who provided the service. The charge 428 imposed by the provider may be considered to be part of the specification of the service or of the results of the adjudication, which also includes an identification of any amount that might be excluded from coverage 432 as a result of the governing policy, the amount paid by the patient as a copayment 436 at the time of service, and the level of benefit 440 provided for the service. It is often the case that medical insurance policies specify a percentage benefit to be applied to service amounts that are reasonable and customary. The type of information included in this example of a standard EOB statement 400 is generally adequate to understand how such a policy was applied in adjudicating the claim. The payment amount 444 that results from adjudication of the claim in this way is specified for each service that was rendered., with the EOB statement 400 also including a total 452 for the amount paid as a result of adjudication of the claim.

In addition to this textual information, organized according to the separate fields in the layout of the EOB statement 400 to ease understanding by human readers, the example in FIG. 4 also illustrates how an optically readable code may be included. Merely by way of illustration, it is shown as a linear bar code 448 that is specified for each of the services described by the EOB statement 400. Because the optically readable code will be read by a machine, the information from the different fields may be concatenated with some descriptor used to separate the fields (in this case, the bar code for ""), enabling the reading machine to parse the field information. Automated reading of a bar code or other optically readable code in this way significantly simplifies the task of extracting relevant information from the EOB statement 400** when needed.

While the example of FIG. 4 shows an embodiment in which a plurality of services identified in a single EOB statement 400 are accommodated by providing a corresponding plurality of optically readable codes, this is also not a necessary feature of the invention. In alternative embodiments, a single optically readable code may be used to encode information from all of the services identified by the EOB statement. Use of a single optically readable code in this way further simplifies the task of extracting the relevant information from the statement 400.

Figure 5A:
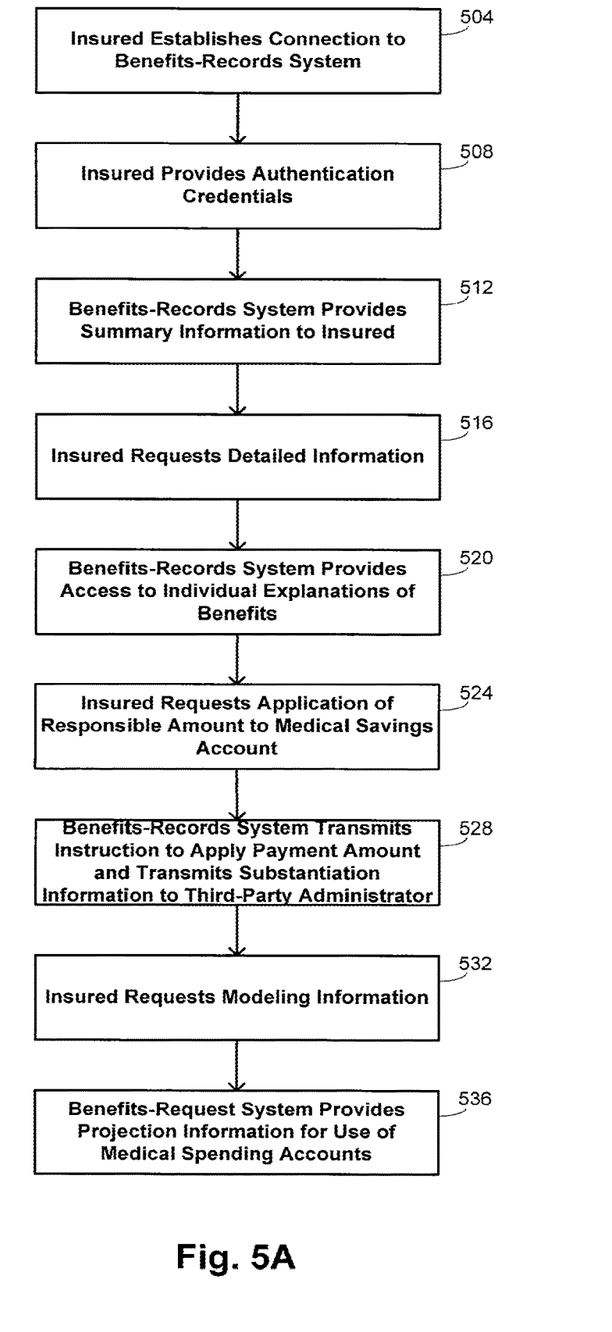
FIG. 5A is a flow diagram summarizing methods of using the benefits-request system by an insured employee.

FIG. 5A is a flow diagram that summarizes some of the functions that may be implemented for insured parties in managing their medical claim information. Such functionality may be provided by arrangements with employers who make such a facility available to their employees as insured parties through an interface with the benefits-records system 104. In some instances, such an interface may include an ability to interface with records maintained by the employer to enable the employee to review medical insurance information as it is maintained internal by the employer.

When the employee wishes to access information maintained by the benefits-records system 104, he or she establishes a connection with the system 104 at block 504. A convenient mechanism for establishing such a connection is through the Internet 108, with the system 104 generating a graphical interface to allow the employee to navigate the different functionalities, although other arrangements may be used in alternative embodiments. Security features will usually be included to verify the identity of the party requesting access to the system 104, usually by requiring the insured party to provide authentication credentials at block 508, such as in the form of a user id and password. Once the insured party has been authenticated, a summary of the information maintained by the benefits-records system for that party may be generated and provided. Such a summary might include an indication of the number of claims that have been submitted and how they were adjudicated or similar summary information.

One function that may be provided by the system 104 to insured parties is the option to review details of the EOB statement information maintained by the system in response to a request at block 516. The detailed EOB information provided to the insured party may take the form of providing access to each of the EOB statements 400 for that party maintained by the system at block 520. This provides the insured party with the ability to review past statements without the need to maintain independent records. This may be a particularly useful feature for insured parties who change employers and/or insurers over time since the centralized repository permits tracking of EOB statement information based on the identity of the insured party without being constrained by who currently employs that party or who currently provides that party with insurance.

The benefit-records interface may then be used by the insured-party employee to request that an amount for which the employee remains responsible be applied to a medical savings account, as indicated at block 524. This amount represents an amount not covered by the insurer for a medical service and which is within the scope of services to which the medical savings account applies. In different embodiments, the medical savings account may comprise a FSA, an HSA, or an HRA. The benefits-records interface responds by transmitting a request at block 528 to apply the amount to the account and by providing a posting of substantiation information to a relevant third-party administrator. Such substantiation information could comprise a copy of the corresponding EOB statement or could comprise information extracted from the corresponding EOB statement in different embodiments.

The interface thus provides a convenient mechanism by which employees may access a complete record of EOB statements to assist in identifying expenses that may be applied to medical spending accounts, and for initiating instructions to make such applications. In addition to simplifying the process for submitting such requests on the part of the employees, the standard format maintained by the benefits-records system 104 permits relevant data to be transmitted to third-party administrators in a consistent fashion that also simplifies conforming to their substantiation requirements.

In instances where the interface is thus integrated with medical-spending-account information, another functionality that may be provided permits modeling projections to be made for the insured party. Within the limits of the medical spending accounts, amounts that are not covered by the insurer for eligible provider services will usually be applied to the medical spending accounts. The benefits-records system 104 may thus easily determine which medical expenses are not being covered by insurance and determine a rate at which they are being paid. This permits projections not only of when a particular medical spending account might be depleted, but also permits an estimate of the appropriate amount to defer to such an account to be made. This is an especially useful feature when the insured-party employee makes use of medical savings accounts whose funds do not roll over from year to year. The request for modeling information is identified at block 532 of FIG. 5A and the generation of a projection response is identified at block 536.

The functionalities described above are merely examples of the types of functions that may be enabled by the information maintained in the central repository. Other examples of functionalities that may be implemented with access to such information will be evident to those of skill in the art after reading the foregoing description.

Figure 5B:
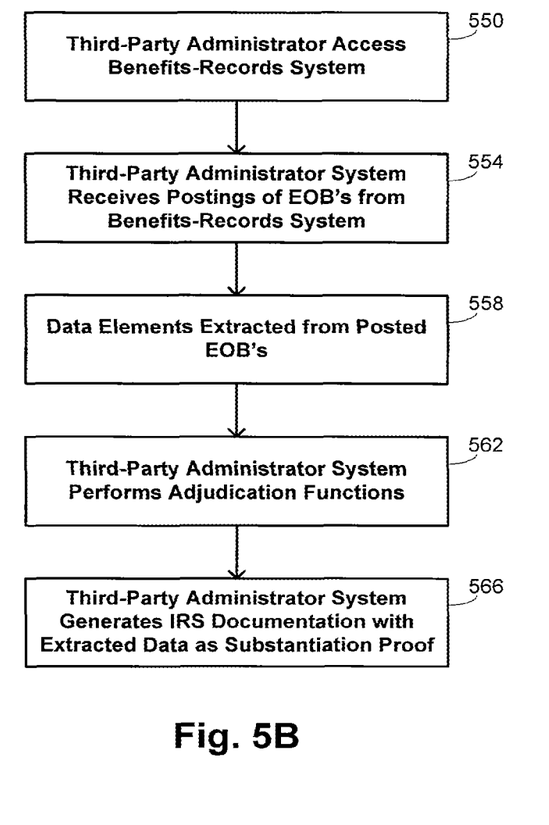
FIG. 5B is a flow diagram summarizing methods of using the benefits-request system by a third-party administrator.

FIG. 5B is a flow diagram that illustrates functionalities that may be implemented to assist third-party administrators of medical spending accounts using the information maintained in the centralized repository. In particular, the information maintained by the benefits-records system 104 may be used as proof under IRS guidelines to comply with substantiation and adjudication requirements when claims have been applied against balances in medical spending accounts. This may advantageously eliminate the need for the insured party to submit a hard-copy paper claim to the third-party administrator, with the insured party instead using the interface with the benefits-records system to provide instructions for applying amounts to medical savings accounts.

The drawing indicates that the third-party administrator may gain access to the benefits-records system 104 at block 550. With such access, postings of the EOB statements may be provided from the benefits-records system 104 to the third-party administrator at block 554. When comprised by the EOB statements, the optically readable codes permit data elements to be extracted efficiently at block 558, allowing the third-party administrator to perform adjudication functions at block 562 and to generate IRS documentation at block 566 with the extracted data as substantiation proof.

Thus, having described several embodiments, it will be recognized by those of skill in the art that various modifications, alternative constructions, and equivalents may be used without departing from the spirit of the invention. Accordingly, the above description should not be taken as limiting the scope of the invention, which is defined in the following claims.

What is claimed is:

1. A system for managing electronic records of benefit information, comprising:
 a communications interface of a benefits-records system configured to establish, via a computer network, a first secure network connection with a first device of a first insurance provider of a plurality of insurance providers;
 the communications interface further configured to receive, via the first secure network connection from the first device of the first insurance provider, a first electronic record comprising, in a first format having a first plurality of fields, data from the plurality of fields indicating an insured employee and a first medical-insurance adjudication explanation for a first service of a first patient generated by the first insurance provider;
 the communications interface further configured to establish, via the computer network, a second secure network connection with a second device of a second insurance provider of the plurality of insurance providers;
 the communications interface further configured to receive, via the second secure network connection from the second device of the second insurance provider, a second electronic record comprising, in a second format having a second plurality of fields different from the first format, data from the plurality of fields indicating the insured employee and a second medical-insurance adjudication explanation for a second service of a second patient generated by the second insurance provider, the second patient different from the first patient;
 the communications interface further configured to receive, via the computer network from a third device of the insured employee, a fourth electronic record comprising, in a third format, data indicating the insured employee and a third medical-insurance adjudication explanation for a third service generated by a device of a third insurance provider;
 the communications interface further configured to transmit, via the computer network, the first electronic record, the second electronic record, and the fourth electronic record to one or more devices designated by request of insured party;
 a processor of the benefits-records system configured to:
  identify the first format of the first electronic record based on an identity of the first insurance provider;
  extract, based on the provided information defining the first format of the first insurance provider, data from the first electronic record corresponding to the provided information;
  provide, based on unidentified one or more portions of first format, an interface configured to receive user input for the first electronic record;
  obtain an indication of an unpaid expense determined from adjudication of a medical-insurance claim adjudicated by the first insurance provider;
  convert, using a mapping of data extracted from the first electronic record and the user input received from the interface, the first electronic record in the first format into a common format configured for the benefits-records system that is common to each of the plurality of insurance providers;
  store the converted first electronic record in a storage device of the benefits-records system, the benefits-records system configured with a data repository that maintains electronic records in the common format;
  identify the second format of the second electronic record based on an identity of the second insurance provider, the second format different from the first format;
  convert, using the mapping of data extracted from the second electronic record and the user input received from the interface, the second electronic record in the second format into the common format;
  convert, using the mapping of data extracted from the fourth electronic record and the user input received from the interface, the fourth electronic record in the third format into the common format;
  generate, using the converted first electronic record, the converted second electronic record, and the converted fourth electronic record, a third electronic record for a single explanation of benefits comprising, in a single optically readable bar code that concatenates information from the first plurality of fields and the second plurality of fields with a descriptor of the optically readable bar code, data indicating (i) the first medical-insurance adjudication explanation for the first service of the first patient received, by the benefits-records system, in the first format via the first secure network connection with the first device of the first insurance provider, (ii) the second medical-insurance adjudication explanation for the second service of the second patient received, by the benefits-records system, in the second format via the second secure network connection with the second device of the second insurance provider, (iii) the third medical-insurance adjudication explanation, and (iv) the indication of the unpaid expense associated with one or more medical-insurance claims in the third electronic record for the single explanation of benefits; and
  transmit, to a fourth device of the insured employee, the third electronic record for the single explanation of benefits in the single optically readable bar code with the descriptor, wherein the fourth device is configured to scan the single explanation of benefits and automatically extract, from the single optically readable bar code, data indicating (i) the first medical-insurance adjudication explanation for the first service of the first patient received, (ii) the second medical-insurance adjudication explanation for the second service of the second patient, (iii) the third medical-insurance adjudication explanation, and (iv) the indication of the unpaid expense associated with the one or more medical-insurance claims in the third electronic record for the single explanation of benefits.

2. The system of claim 1, wherein the processor is further configured to:
 store, in the data repository of the storage device, the first electronic record in the common format; and
 store, in the data repository of the storage device, the second electronic record in the common format.

3. The system of claim 1, wherein the processor is further configured to:
   store, in the data repository of the storage device, the first electronic record in the common format;
   store, in the data repository of the storage device, the second electronic record in the common format; and
   retrieve, from the data repository of the storage device, responsive to the request, the stored first electronic record in the common format and the stored second electronic record in the common format to generate the third electronic record for the single explanation of benefits.

4. The system of claim 1, wherein the processor is further configured to:
   convert at least a part of the first medical-insurance adjudication explanation into a first optically readable bar code; and
   convert at least a part of the second medical-insurance adjudication explanation into a second optically readable bar code.

5. The system of claim 1, wherein:
   the communications interface is further configured to receive, in a plurality of formats, a plurality of medical-insurance adjudication explanations comprising a specification of the medical-insurance claim submitted to the first insurance provider and identifying an adjudication decision of the medical-insurance claim, the plurality of formats including at least one of a portable document format, facsimile transmission, a scanned statement in an electronic format, or a textual format of a short-message-service; and
   the processor is further configured to store, in the data repository, each of the plurality of medical-insurance adjudication explanations in the common format.

6. The system of claim 1, wherein one of the first format or the second format comprises an optically readable bar code.

7. The system of claim 1, wherein the processor is further configured to:
   receive, from the third device of the insured employee, a request to apply a payment amount to a medical spending account corresponding to an expense associated with a medical-insurance claim in the third electronic record for the single explanation of benefits.

8. The system of claim 7, wherein the medical spending account comprises at least one of a flexible spending account, a health savings account, or a health reimbursement account.

9. The system of claim of claim 1, wherein:
   the communications interface is configured to receive, via the computer network from the third device of the insured employee, the fourth electronic record comprising, in the third format, data indicating the insured employee and the third medical-insurance adjudication explanation for the third service generated by a device of the third insurance provider; and
   the processor generates the third electronic record for the single explanation of benefits with data indicating the first medical-insurance adjudication explanation, the second medical-insurance adjudication explanation, and the third medical-insurance adjudication explanation.

10. A system for managing electronic records of benefit information, comprising:
   a communications interface of a benefits-records system configured to receive, via a first secure network connection over a computer network from a first device of a first insurance provider, a first electronic record for a first patient, the first electronic record comprising, in a first format having a first plurality of fields, a first medical-insurance adjudication explanation for a first service and identifying an insured employee;
   the communications interface of the benefits-records system further configured to receive, via a second secure network connection from a second device of a second insurance provider different from the first insurance provider, a second electronic record for a second patient different from the first patient, the second electronic record comprising, in a second format having a second plurality of fields different from the first format, a second medical-insurance adjudication explanation for a second service different from the first service and an identification of the insured employee;
   the communications interface further configured to receive, via the computer network from a third device of the insured employee, a fourth electronic record comprising, in a third format, data indicating the insured employee and a third medical-insurance adjudication explanation for a third service generated by a device of a third insurance provider;
   the communications interface further configured to transmit, via the computer network, the first electronic record, the second electronic record, and the fourth electronic record to one or more devices designated by request of insured party;
   a processor of the benefits-records system configured to:
      identify the first format of the first electronic record based on an identity of the first insurance provider;
      extract, based on the provided information defining the first format of the first insurance provider, data from the first electronic record corresponding to the provided information;
      provide, based on unidentified one or more portions of first format, an interface configured to receive user input for the first electronic record;
      obtain an indication of an unpaid expense determined from adjudication of a medical-insurance claim adjudicated by the first insurance provider;
      identify the second format of the second electronic record based on an identity of the second insurance provider, the second format different from the first format;
      encode, based on a mapping of the first format to a common format and the second format to the common format, and the third format to the common format, for a third electronic record for a single explanation of benefits, a single optically readable bar code that concatenates information from the first plurality of fields and the second plurality of fields with a descriptor of the optically readable bar code, the single optically readable bar code comprising: (i) the first medical-insurance adjudication explanation for the first service of the first patient received, by the benefits-records system, in the first format via the first secure network connection with the first device of the first insurance provider, (ii) the second medical-insurance adjudication explanation for the second service of the second patient received, by the benefits-records system, in the second format via the second secure network connection with the second device of the second insurance provider, (iii) the third medical-insurance adjudication explanation, and (iv) the indication of the unpaid expense associated with one or more medical-insurance claims in the third electronic record for the single explanation of benefits;

generate a single electronic explanation of benefits record for the insured employee comprising the encoded single optically readable bar code; and transmit, to a fourth device of the insured employee, the single electronic explanation of benefits record in the encoded single optically readable bar code with the descriptor to cause the fourth device to scan the single explanation of benefits and automatically extract, from the encoded single optically readable bar code, the data indicating (i) the first medical-insurance adjudication explanation for the first service of the first patient received, (ii) the second medical-insurance adjudication explanation for the second service of the second patient, (iii) the third medical-insurance adjudication explanation, and (iv) the indication of the unpaid expense associated with the one or more medical-insurance claims in the third electronic record for the single explanation of benefits.

11. The system of claim 10, further comprising:
a storage device including a data repository that maintains electronic records in the common format,
wherein the processor is further configured to:
    store, in the data repository of the storage device, the first electronic record in the common format; and
    store, in the data repository of the storage device, the second electronic record in the common format.

12. The system of claim 10, further comprising:
a storage device including a data repository that maintains electronic records in the common format,
wherein the processor is further configured to:
    store, in the data repository of the storage device, the first electronic record in the common format;
    store, in the data repository of the storage device, the second electronic record in the common format; and
    retrieve, from the data repository of the storage device, responsive to the request, the stored first electronic record in the common format and the stored second electronic record in the common format to generate the single electronic explanation of benefits record.

13. The system of claim 10, wherein the processor is further configured to:
    convert at least a part of the first medical-insurance adjudication explanation into a first optically readable bar code; and
    convert at least a part of the second medical-insurance adjudication explanation into a second optically readable bar code.

14. The system of claim 10, wherein:
the communications interface is further configured to receive, in a plurality of formats, a plurality of medical-insurance adjudication explanations comprising a specification of the medical-insurance claim submitted to the first insurance provider and identifying an adjudication decision of the medical-insurance claim, the plurality of formats including at least one of a portable document format, facsimile transmission, a scanned statement in an electronic format, or a textual format of a short-message-service; and
the processor is further configured to store, in a data repository of a storage device, each of the plurality of medical-insurance adjudication explanations in the common format.

15. The system of claim 10, wherein one of the first format or the second format comprises an optically readable bar code.

16. The system of claim 10, wherein the processor is further configured to:
    receive, from the third device of the insured employee, a request to apply a payment amount to a medical spending account corresponding to an expense associated with a medical-insurance claim in the third electronic record for the single explanation of benefits.

17. The system of claim 16, wherein the medical spending account comprises at least one of a flexible spending account, a health savings account, or a health reimbursement account.

18. The system of claim 10, wherein:
the communications interface is further configured to receive, via the computer network from the third device of the insured employee, the fourth electronic record comprising, in the third format, data indicating the insured employee and the third medical-insurance adjudication explanation for the third service generated by the fourth device of the third insurance provider; and
the processor generates the third electronic record for the single explanation of benefits using data indicating the first medical-insurance adjudication explanation, the second medical-insurance adjudication explanation, and the third medical-insurance adjudication explanation.

* * * * *